US 6,595,037 B2

(12) United States Patent
McGinley

(10) Patent No.: US 6,595,037 B2
(45) Date of Patent: Jul. 22, 2003

(54) PORTABLE ODOR DETECTING AND MEASURING DEVICE

(76) Inventor: Charles M. McGinley, 13701 - 30th Street Cir. North, Stillwater, MN (US) 55082

( * ) Notice: Subject to any disclaimer, the term of this patent is extended or adjusted under 35 U.S.C. 154(b) by 44 days.

(21) Appl. No.: 09/922,975

(22) Filed: Aug. 7, 2001

(65) Prior Publication Data

US 2003/0033852 A1 Feb. 20, 2003

(51) Int. Cl.⁷ .............................................. G01N 33/497
(52) U.S. Cl. ...................... 73/23.34; 73/23.34; 73/23.3; 422/83; 422/84
(58) Field of Search .............................. 73/23.34, 23.3; 422/83, 84

(56) References Cited

U.S. PATENT DOCUMENTS 2,484,217 A * 10/1949 Gardenier ................... 600/532
5,081,871 A * 1/1992 Glaser ....................... 73/863.23
6,018,984 A 2/2000 McGinley et al.

OTHER PUBLICATIONS

Scentometer: An Instrument For Field Odor Measurement by Barneby & Sutcliffe Corporation, 3 pages, date uncertain.
Objective Odor Pollution Control Investigations by Huey, et al., 4 pages Journal of Air Pollution Control Ass'n Dec. 1960.
Odor Control With Activated Carbon, Barneby–Cheney Co., 2 pages APCA Journal vol. 13, No. 4.

* cited by examiner

*Primary Examiner*—Daniel S. Larkin
*Assistant Examiner*—André K. Jackson
(74) *Attorney, Agent, or Firm*—Jacobson and Johnson

(57) ABSTRACT

A portable olfactometer for sensing and measuring odors by sniffing has a barrel which carries selectively different D/T ratios of odorous air to a nose mask and has a selective set of inserts for providing different D/T ratios at the input to the barrel.

12 Claims, 4 Drawing Sheets

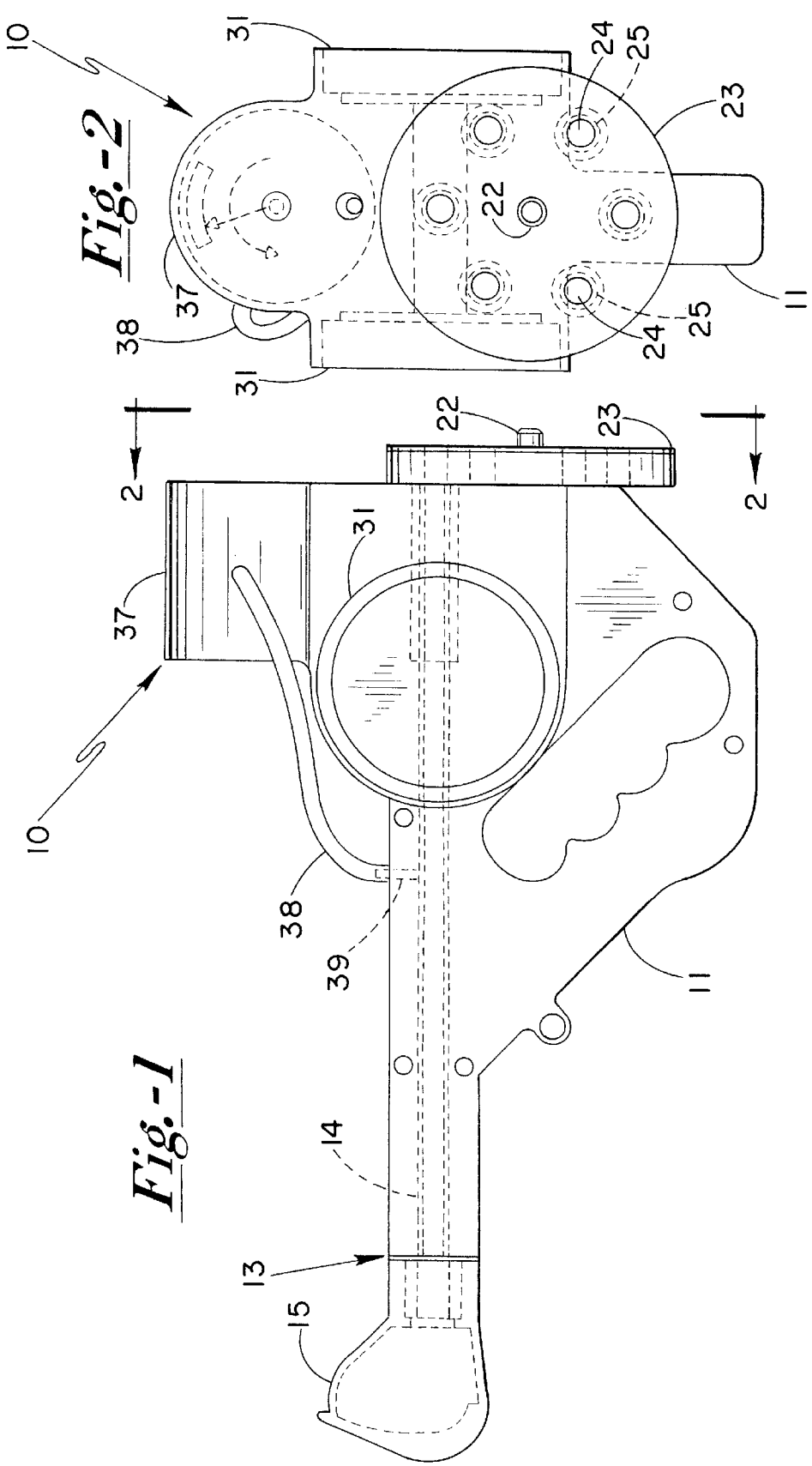

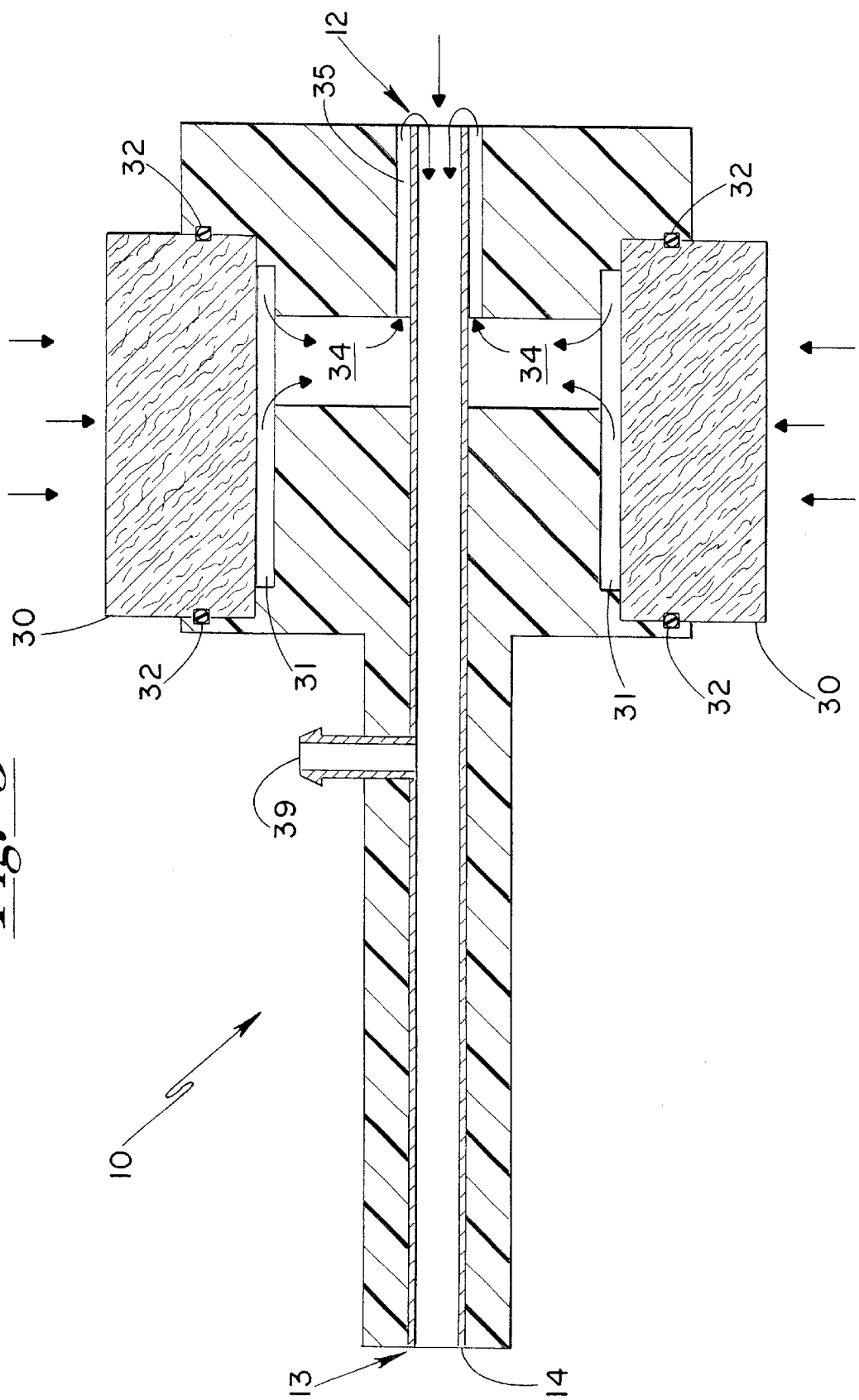

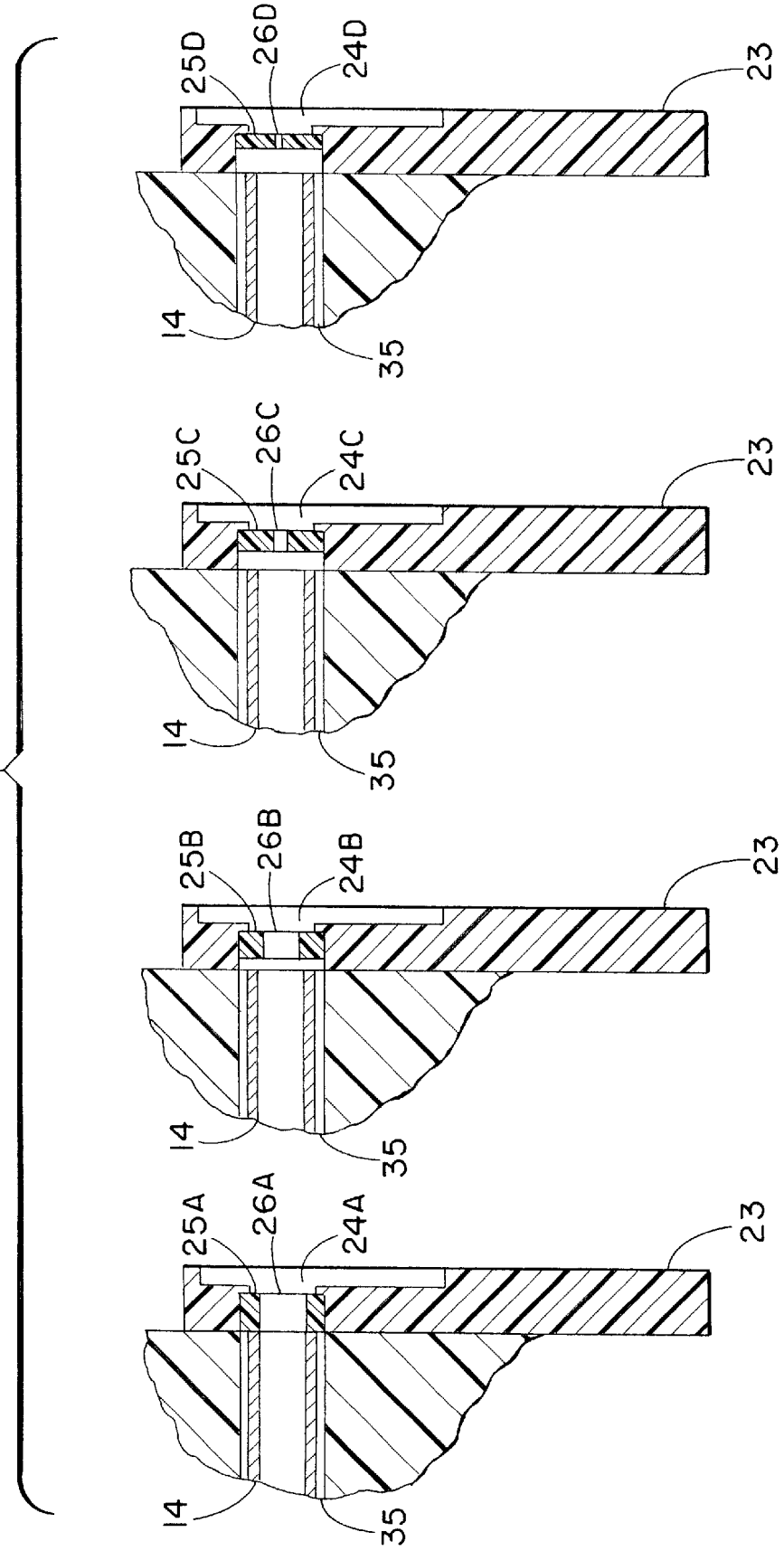

PORTABLE ODOR DETECTING AND MEASURING DEVICE

FIELD OF THE INVENTION

This invention relates to sensing or detecting and measuring odors and in particular is aimed at detecting and measuring odors in the field, i.e., not under laboratory conditions.

DESCRIPTION OF THE PRIOR ART

U.S. Pat. No. 6,018,984 and an earlier U.S. Pat. No. 3,902,851, referenced in the '984 patent, discuss and describe in considerable detail olfactometers for detecting and measuring air polluting odors. These devices are quite sophisticated and are used as laboratory instruments in which the sample odors are fed from a container into the olfactometer in various dilution ratios commonly known as D/T, ("Dilution to Threshold"). In the device described in the '984 patent odorous air is fed to a venturi mixing nozzle through various branches containing solenoid operated valves and different sized orifices for mixing with odor-free air to provide various D/T levels. The prior art also includes a device for field use for detecting and measuring air pollution in the form of a Scentometer manufactured and sold by Barnebey and Sutcliffe Corporation (now Barnebey-Cheney Company). The Scentometer essentially is a rectangular clear plastic box containing two chambers of activated carbon, two nasal outlet ports for sniffing separately into each nostril, two air inlets (one for each activated carbon bed) and six odorous air inlets of different sizes, to provide the various D/T ratios, which are directly connected with a mixing chamber and the nasal outlets. Odorless or odor-free air is obtained by air being drawn through beds of carbon and filtered air is mixed with the odorous air. The Scentometer user follows the generally accepted or standard practice of detecting and measuring the odor by first sniffing with the smallest odorous air inlet opening (lowest D/T ratio) and then successively opening the next largest odorous air inlet until the user or tester finds that an odor is discernible. The size of the opening or orifice for the odor inlet at which the odor is discernible then indicates to the tester the approximate concentration of the odor or the odor level. In the past, conventionally D/T was calculated by dividing the volume of odor free air by the volume of odorous air but more recently, the more sophisticated laboratory instruments calculate D/T by dividing the total air flow volume by the volume of odorous air.

SUMMARY OF THE INVENTION

The present invention utilizes a fairly small lightweight housing suitable to be hand carried so it is convenient to use in the field. The housing contains a hollow tube or barrel open at both ends. One end is the air input end, the other is the air output end. Odorous air, i.e., the ambient polluted air, enters the inlet end and travels down the tube to the outlet end to which is attached a nose mask for directing the air to the sensor or tester's nostrils when the user inhales. The nose mask also has an outlet opening and there are check valves for the nose mask inlet openings and outlet openings so that the former is open and the latter closed when the user inhales and vice versa. Odorless or odor-free air is obtained from ambient air passing through a multi-media filter and is fed into the housing where it is mixed with the polluted or odorous air at the inlet end of the barrel. In the preferred form a disk having a series of apertures is rotatably attached to the housing at the air inlet end of the barrel with the apertures containing inserts having respectively different sized orifices and thicknesses. The disk is rotated by the user to bring each aperture successively to a position opposite the inlet opening of the barrel and sniffs as necessary to draw the air mixture into the nose mask. The setting at which the odor is discernible gives the D/T ratio. Filtering the ambient air through a multi-media filter instead of through a carbon filter as in the Scentometer provides a more universal and more complete filtering of odors out of the ambient air that is used to mix with the odorous air. Preferably these filters are commercially available devices which can be releasably secured to the housing in some convenient fashion such as snapping or press-fitting or threading them into place. They are suitably sealed to prevent any leakage of any of the polluted air into the odor-free air passageway yet they are attached in some fashion so they can be easily and quickly removed and replaced as necessary.

BRIEF DESCRIPTION OF THE DRAWINGS

FIG. 1 is a plan view or a side view of a preferred embodiment of the invention;

FIG. 2 is an end view;

FIG. 3 is a lengthwise partial section view;

FIG. 5 is a detail diagramatic illustration of various sized orifices used in to obtain the desired D/T ratios in operation of the invention.

DESCRIPTION OF THE PREFERRED EMBODIMENTS

Figure 4:
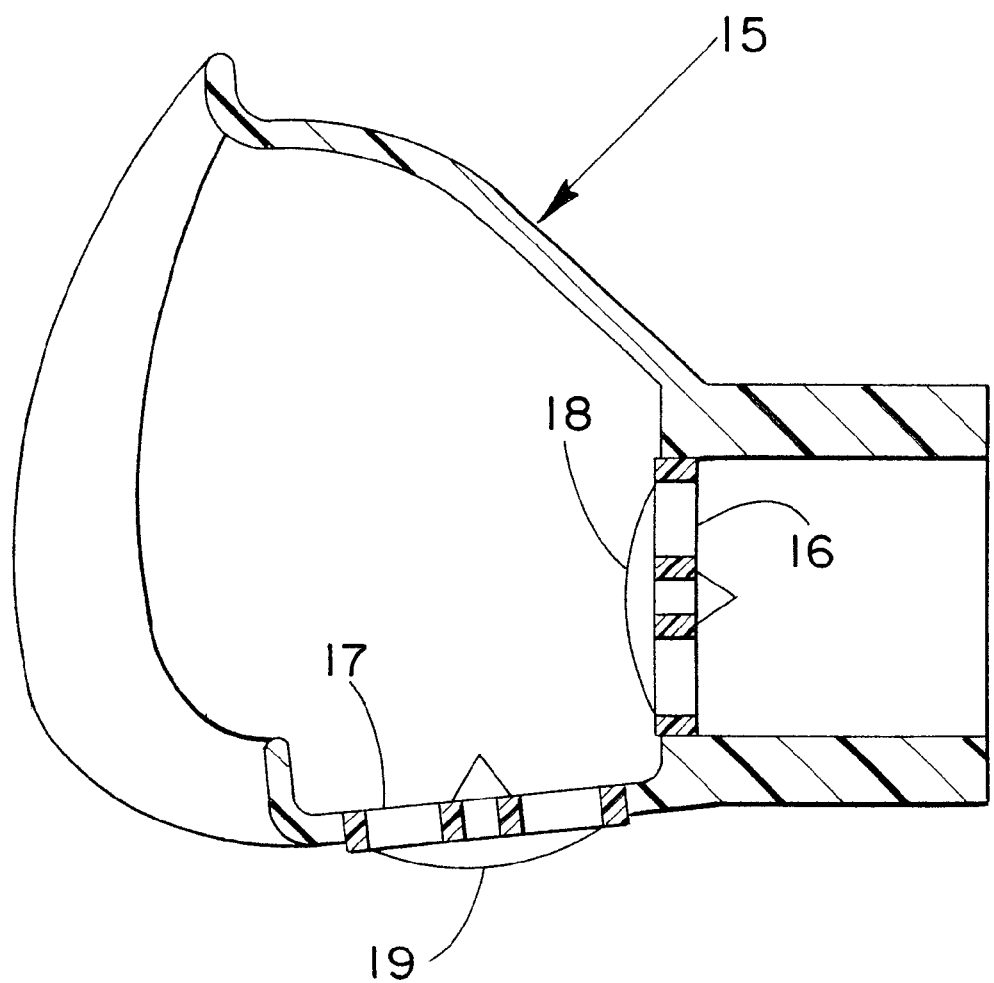
FIG. 4 is an illustration of a nose mask.

Housing 10 is molded out of some suitable material that is fairly light in weight so it is easily carried. Of course it must be made out of material that has characteristics which are such that it is inert to any of the polluting odors that it is used to detect and measure and further, does not produce any odors which could interfere with the readings. The housing has a handle 11 and for reference purposes has an air input end designated generally by reference numeral 12 and an air output end designated generally by reference numeral 13. The housing contains an elongated rigid hollow tube or barrel 14 which must be made of a material such as Teflon or stainless steel which is inert to any of the odors encountered and which does not produce any of its own odors. At the air output end 13 a nasal mask 15 is removably attached to make air communication with the outlet end of barrel 14. Nasal mask 15 has an inlet opening 16 in air communication with the outlet end of barrel 14 and an outlet opening 17. Each of these openings has a check valve 18 and 19, respectively, (FIG. 4). In use, the operator or tester places the nose mask 15 over his or her nose fairly securely and inhales or sniffs to bring air through barrel 14 into the nasal mask through opening 16. In conventional fashion check valve 18 opens to permit air to enter into the nose mask and check valve 19 remains closed. When the operator discharges the air from his or her lungs the exhaled air is discharged through opening 17 with check valve 19 opening and check valve 18 remaining closed.

Rotatably mounted at the input air end 12 of housing 10 in some conventional fashion, such as by a pivot pin 22, is a disk 23. Disk 23 has a series of circularly or circumferentially spaced circular apertures 24 which are located so that disk 23 can be rotated about pivot pin 22 to bring each of the apertures 24 directly opposite the air input end of sleeve or barrel 14 so that the aperture is then in air communication with barrel 14. Disk 23 has a latching feature, not shown, of a conventional nature which can be overridden by the user manually turning the disk. The latching mechanism ensures that each of the apertures 24 when brought into place is located exactly opposite the open input end of barrel 14. Typically, with no limitation intended, the latching mechanism may constitute a spring-loaded ball which engages an indentation on disk 23.

Each of the apertures 24 contains an insert 25 which seals off the aperture against the flow of any air through the aperture except for an orifice or small opening 26 at about the general center of the insert 25. FIG. 5 illustrates samples of the nature of the respective inserts in the respective apertures. Typically the disk has six different apertures which, along with the thickness of the insert, (as will be explained later) provides six different D/T ratios. This seems to be fairly conventional in order to obtain a fairly accurate reading of the odor. Except for practical limitations the number of apertures on the disk may be a matter of choice.

FIG. 3 is a partial section view of the housing to illustrate how the odor-free air enters into the housing in order to be mixed with odorous air to produce the various D/T ratios which are used to obtain a fairly accurate reading of the degree of pollution caused by the odor. A pair of multimedia filter cartridges 30 which are conventionally in disk-like shape, similar to a hockey puck, are suitably mounted in respective recesses 31 in housing 10. Filter cartridges are conventional and are commercially available. Examples of these are Cartridge S10, PN 7276 by 3M Company and Cartridge GME, PN 492772 by MSA Company. The cartridges 30 might be threaded into place within their respective recesses 31 or may be press-fitted into place or attached in some fashion that will allow them to be removed and replaced as necessary from time to time. In any event, the cartridges 30 are sealed in their recesses such as by O-rings 32 to prevent any air or gas from entering into the recesses around the outside of the filter cartridges. A pair of radial air passageways 34 in housing 10 allow the filtered air from the filter cartridges 30 to flow radially inward toward the outside of barrel 14 and continue toward the inlet end 12 of barrel 14 along the outside of barrel 14 through an annular passageway 35 coaxial with barrel 14.

FIG. 5 is a functional illustration or diagram to illustrate the manner in which the odor free air is mixed with the odorous air and inputted to the input end of a barrel 14 to produce the respective D/T ratios to arrive at a fairly accurate reading of the degree of odor air pollution. Typically, but with no intent to be limitive, six different D/T ratios generally are used in order to arrive at a fairly accurate reading. Only four examples are shown in FIG. 5 for illustrative purposes. Leftmost illustrates one extreme, i.e., the situation where only odorous air is allowed to enter the input end of barrel 14 and the odor-free air is blocked out which results in a D/T ratio of 0. Orifice 26A of insert 25A provides the largest opening for the odorous air and the thickness of insert 25A is such that it closes off the end of passageway 35 so that no odor-free air is mixed with the odorous air which flows down barrel 14 to nasal mask 15. The other extreme, not shown, has an insert which has no orifice and is quite thin so only odor-free air and no odor is allowed to enter the nasal mask. In practice, the operator may and usually will use the "no odor" position between each odor presentation in order to refresh the nostrils between each odor test. Rightmost illustrates a high D/T ratio in which orifice 26D is quite small so that only a small amount of odorous air is allowed to enter the input end of barrel 14. The insert 25D is quite thin so that the end of annular passageway 35 is substantially open so that a large amount of odorless air mixes with the odorous air to produce a high D/T ratio. In between are illustrations of intermediate settings for intermediate D/T ratios. The size of orifice 26 and the thickness of insert 25 are directly related; i.e., the larger the orifice opening (to allow more odorous air), the thicker the insert (to reduce the amount of odorless air). Examples of dimensions for the orifice and the insert thickness for each of the desired D/T ratios, no limitation intended, are shown in Table 1 for use with a barrel 14 having an inner diameter of about 0.364 inch and an outer diameter of about 0.540 inch and an annular passageway 35 having an outer diameter of about 0.750 inch with the outside of insert 25 about 0.283 inch from the end of barrel 14. Naturally, other dimensions can be used to produce the same or different D/T ratios, as desired.

TABLE 1

| Orifice Size | Insert Thickness | Ratio |
|---|---|---|
| .364 | .283 | (All Odor) |
| .300 | .180 | D/T = 1 |
| .120 | .140 | D/T = 7 |
| .050 | .110 | D/T = 100 |

Typically, in operation, after doing whatever is necessary to make sure that there are no lingering odors within cartridge or mask 15, the user with nose mask 15 placed snugly over his or her nose moves or rotates disk 23 so that the aperture containing the smallest orifice 26, and, correspondingly the thinnest insert 25, is in position opposite the inlet opening of barrel 14 and sniffs to draw air into the nostrils. The operator normally takes a number of sniffs and exhales each one to make sure that a suitable sample of a mixture of odor-free and odorous air is being inhaled into the nostrils. As explained earlier, the respective checkvalves 18 and 19 respond in the proper manner so that only the mixture is inhaled and the exhaled air goes out the outlet opening and not back into the barrel 14. In order to assure that the user is inhaling a sufficient volume of mixture of odor-free and odorous air a meter 37 may be attached to the housing and coupled in some fashion to barrel 14 in order to give a visual reading of air flow rate being inhaled. If initially there is no discernible odor, then the operator rotates disk 23 to place the opening or aperture 24 with the next larger orifice and thicker insert opposite the end of barrel 14 and repeats the procedure. This continues on until an odor is discernible to the operator. The setting at which the odor is discernible gives the D/T ratio. Ordinarily the operator repeats the tests over a period of time and then records the results. By providing a correlation between the size of the orifice and the thickness of the insert for each setting the air flow rate down barrel 14 can be kept the same for all settings with differing ratios of odor-free and odorous air. The multimedia filters 30 are much more effective than the carbon filter of the earlier Scentometer because they are able to remove various odor contaminants that were not filtered out by the carbon filters.

Meter 37 preferably has a dial face, not shown, to give a visual indication to the operator of the air flow rate in barrel 14 to the nasal mask. Suitable tubing 38 attached at one end to meter 37 is connected at the other end to a pressure tap or port 39 on barrel 14. Preferably the operator inhales and views meter 37 to make sure a prescribed air flow rate is drawn down barrel 14.

I claim:

1. A portable device for detecting and measuring odors by sniffing, comprising:

a housing of a size and weight suitable for carrying by hand;

a first air passageway in said housing having an inlet opening at one end and an outlet opening at the other end;

a second air passageway in said housing separate from said first air passageway, said second air passageway having an outlet end in air communication with said first passageway at said inlet opening of said first air passageway;

means for feeding odorless air into said second air passageway;

means at said first air passageway inlet opening for allowing selectively different amounts of odorless air from said second air passageway and odorous air into the inlet opening of said first passageway; and a nose mask for placing over a user's nose, said nose mask removably attached to said housing and having an intake opening in air communication with the outlet opening of said first passageway for permitting air to be drawn into said nose mask from said first passageway when the user inhales.

2. A portable odor detecting and measuring device as described in claim 1 wherein said second air passageway is annular and concentric with said first air passageway.

3. A portable odor detecting and measuring device as described in claim 2 wherein said means for allowing different amounts of odorous air to enter the first passageway comprises:

a ratio selector member having a multiplicity of apertures, said member movably attached to said housing for manually selectively placing said apertures into air communication with the inlet end of said first passageway; and an insert in each of said apertures having a preselected size orifice for selectively restricting the amount of odorous air entering the inlet opening of said first passageway.

4. A portable odor detecting and measuring device as described in claim 3 wherein:

the insert in each of said apertures has a preselected thickness for selectively restricting the amount of odorless air entering the inlet opening of said first passageway from said second air passageway.

5. A portable odor detecting and measuring device as described in claim 1 wherein said means for feeding odorless air into said second air passageway comprises:

a third air passageway in said housing having an outlet in air communication with said second passageway and having an air inlet; and filter means at the inlet of said third passageway for filtering out any odor in the air entering said third passageway.

6. A portable odor detecting and measuring device as described in claim 1 wherein said nose mask has an exhale opening and check valves at each of said intake and exhale openings.

7. A portable odor detecting and measuring device as described in claim 3 wherein said ratio selector member comprises a generally circular disc rotatably attached to said housing with said apertures spaced circumferentially for selectively placing each aperture at the inlet end of said first passageway.

8. A portable odor detecting and measuring device as described in claim 1 further including an air flow detecting device mounted on the exterior of said housing coupled to said first air passageway for visually indicating air flow rate in said first air passageway.

9. A portable odor detecting and measuring device as described in claim 1 wherein said means for allowing different amounts of odorous air and odorless air to enter the first passageway comprises:

a ratio selector member having a multiplicity of apertures, said member movably attached to said housing for manually selectively placing said apertures into air communication with the inlet end of said first passageway; and an insert in each of said apertures, said insert having a preselected size orifice for selectively restricting the amount of odorous air entering the inlet opening of said first passageway and a preselected thickness for selectively restricting the amount of odorless air entering the inlet opening of said first passageway from the outlet end of said second air passageway.

10. A portable odor detecting and measuring device as described in claim 9 wherein said means for feeding odorless air into said second air passageway comprises:

a third air passageway in said housing having an outlet in air communication with said second passageway and having an air inlet; and filter means at the inlet of said third passageway for filtering out any odor in the air entering said third passageway.

11. A portable odor detecting and measuring device as described in claim 1 wherein said nose mask has an exhale opening and check valves at each of said intake and exhale openings.

12. A portable odor detecting and measuring device as described in claim 9 wherein said ratio selector member comprises a generally circular disc rotatably attached to said housing with said apertures spaced circumferentially on said disc for selectively placing each aperture at the inlet end of said first passageway.

* * * * *